United States Patent
Armstrong et al.

(10) Patent No.: US 10,881,640 B2
(45) Date of Patent: *Jan. 5, 2021

(54) TOPICAL PHARMACEUTICAL COMPOSITIONS FOR TREATMENT OF PILONIDAL SINUS WOUNDS

(71) Applicant: S.L.A. PHARMA AG, Liestal (CH)

(72) Inventors: David Nigel Armstrong, Lawrenceville, GA (US); Justin Slagel, Watford (GB)

(73) Assignee: S.L.A. PHARMA AG, Liestal (CH)

(*) Notice: Subject to any disclaimer, the term of this patent is extended or adjusted under 35 U.S.C. 154(b) by 427 days.

This patent is subject to a terminal disclaimer.

(21) Appl. No.: 15/234,084

(22) Filed: Aug. 11, 2016

(65) Prior Publication Data

US 2016/0346253 A1 Dec. 1, 2016

Related U.S. Application Data

(63) Continuation of application No. 13/834,281, filed on Mar. 15, 2013, now Pat. No. 10,653,671, which is a continuation-in-part of application No. 12/834,198, filed on Jul. 12, 2010, now Pat. No. 9,655,883, which is a continuation of application No. 10/525,208, filed as application No. PCT/GB03/03692 on Aug. 22, 2003, now abandoned.

(60) Provisional application No. 60/406,351, filed on Aug. 26, 2002.

(51) Int. Cl.

| | |
|---|---|
| *A61K 31/685* | (2006.01) |
| *A61K 31/4164* | (2006.01) |
| *A61K 9/00* | (2006.01) |
| *A61K 31/192* | (2006.01) |
| *A61K 31/24* | (2006.01) |
| *A61K 31/245* | (2006.01) |
| *A61K 31/355* | (2006.01) |
| *A61K 31/407* | (2006.01) |
| *A61K 31/4166* | (2006.01) |
| *A61K 31/545* | (2006.01) |
| *A61K 31/573* | (2006.01) |
| *A61K 31/60* | (2006.01) |
| *A61K 31/65* | (2006.01) |
| *A61K 33/30* | (2006.01) |
| *A61K 45/06* | (2006.01) |
| *A61K 9/06* | (2006.01) |
| *A61K 47/06* | (2006.01) |
| *A61K 47/44* | (2017.01) |

(52) U.S. Cl.
CPC ........ *A61K 31/4164* (2013.01); *A61K 9/0014* (2013.01); *A61K 9/0031* (2013.01); *A61K 9/06* (2013.01); *A61K 31/192* (2013.01); *A61K 31/24* (2013.01); *A61K 31/245* (2013.01); *A61K 31/355* (2013.01); *A61K 31/407* (2013.01); *A61K 31/4166* (2013.01); *A61K 31/545* (2013.01); *A61K 31/573* (2013.01); *A61K 31/60* (2013.01); *A61K 31/65* (2013.01); *A61K 33/30* (2013.01); *A61K 45/06* (2013.01); *A61K 47/06* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 4,784,994 | A | 11/1988 | Romer et al. |
| 4,957,918 | A | 9/1990 | Martin et al. |
| 5,248,505 | A | 9/1993 | Garwin |
| 5,948,400 | A | 9/1999 | Brett |
| 2003/0092754 | A1 | 5/2003 | Nishumuta et al. |

FOREIGN PATENT DOCUMENTS

| | | |
|---|---|---|
| CN | 1291484 | 4/2001 |
| EP | 0 386 960 | 9/1990 |
| RU | 119610523913 | 6/1998 |
| UA | 53946 | 2/2003 |
| WO | WO 92/09272 | 11/1992 |

OTHER PUBLICATIONS

Roa et al. (An Appraisal of the Healing Profiles of Oral and External (Gel) Metronidazole on Partial Thickness Burn Wounds. Indian Journal of Pharmacology 2000; 32: 282-287).*

Huber, L. "Role of Klion Ointment in the Treatment of Crural Ulcer." Therapia Hungarica, 39(3), 148-150 (1991).

Jakobovits, J. et al. "Metronidazole therapy for Crohn's disease and associated fistulae." American Journal of Gastroenterology, 1984, vol. 79, No. 7, pp. 533-540.

Kryzhanovsky, S.A. et al. Sovremennye Lakarstvennye Preparaty, p. 792, Ripol Classic—Moscow, 2000 & English Translation.

Nygaard, K. et al. "Topical metronidazole treatment in pouchitis." Scandinavian Journal of Gastroenterology, Norway, May 1994, vol. 29, No. 5, (pp. 462-467).

Teknologiya Lekarstvennye Form, edited by Kondrat'jeva, T.C., pp. 282-285 and 314-317 Medisina, Moscow 1991 & English Translation.

Urbanek et al. Vulval Crohns Disease Difficulties in Diagnosis, pp. 211-214, May 21, 1996 (3).

Ursing et al. Metronidazole for Crohn's Disease, Lancet, 1975, 1 (7910) 775-777.

(Continued)

*Primary Examiner* — Layla Soroush
(74) *Attorney, Agent, or Firm* — Tristan A. Fuierer; Marianne Fuierer; Olive Law Group, PLLC

(57) ABSTRACT

A topical composition comprising about 5 wt % to about 12.5 wt % of metronidazole or a pharmacologically acceptable salt thereof in a non-aqueous vehicle. The composition may be used in the treatment of skin damage due to inflammatory skin conditions; thermal, chemical or electrical burns; infections or radiation treatment. One advantage of the composition is that topical administration of metronidazole results in a primarily local effect, and thus, side effects observed from systemic administration are avoided.

12 Claims, No Drawings

(56) References Cited

OTHER PUBLICATIONS

Wahba-Yahev et al. Idopathic lichen planus: Treatment with metronidazole. Journal of the American Academy of Dermatology 33.2 (1995): 301-305.
Willis et al. Metronidazole in prevention and treatment of bacteroids infections after appendicectomy. Br. Med J. Feb. 7, 1976; 1(6005): 318-321.
Rice, Trudy Thompson; "Metronidazole Use in Malodorous Skin Lesions," Rehabilitation Nursing, 1992, pp. 244-245 & 255; vol. 17.
Rao, C. Mallikarjuna et al. An Appraisal of the Healing Profiles of Oral and External (Gel) Metronidazole on Partial Thickness Burn Wounds. Indian Journal of Pharmacology, 2000, 32: 282-287.
Final Office Action, U.S. Appl. No. 14/288,686; dated Nov. 1, 2018.
Parkes, M. et al. "The Management of Severe Crohn's Disease." Aliment Pharmacol Ther, 15(3), 563-573 (2001).
Final Office Action, corresponding to U.S. Appl. No. 14/288,686 dated Apr. 5, 2018.
Seaman, S. "Management of Malignant Fungating Wounds in Advanced Cancer." Seminars in Oncology Nursing, 22(3), 185-193 (2006).
Office Action, corresponding to U.S. Appl. No. 13/834,281, dated Jul. 6, 2017.

\* cited by examiner

TOPICAL PHARMACEUTICAL COMPOSITIONS FOR TREATMENT OF PILONIDAL SINUS WOUNDS

CROSS REFERENCE TO RELATED APPLICATIONS

This application is a Continuation Application and claims priority to U.S. patent application Ser. No. 13/834,281 filed on Mar. 15, 2013, which in turn is a Continuation-in-Part Application of and claims priority to co-pending U.S. patent application Ser. No. 12/834,198, filed on Jul. 12, 2010, which in turn was a Continuation Application and claimed priority to U.S. application Ser. No. 10/525,208, filed Mar. 30, 2006; which is a National Stage Application of PCT/GB2003/003692; filed Aug. 22, 2003; which claims priority to U.S. Provisional Application No. 60/406,351, filed Aug. 26, 2002. All of the above applications are incorporated into the current continuation-in-part application by reference.

BACKGROUND OF THE INVENTION

Technical Field

The present invention relates to a pharmaceutical composition, in particular a topical composition comprising metronidazole or a pharmacologically acceptable salt thereof, for the treatment of skin damage.

Related Art

Metronidazole (or "Flagyl") is a synthetic antibacterial and antiprotozoan antibiotic having the formula 2-methyl-5-nitroimidazole-1-ethanol. Metronidazole possesses not only anti-bacterial properties, but also anti-inflammatory properties, which are less well understood. The medication is used for its anti-inflammatory properties in the treatment of several skin diseases.

However, in its oral and intravenous forms, metronidazole is frequently associated with a number of serious side effects. These negative side effects include GI manifestations, such as nausea, vomiting, a metallic taste in the mouth, or inflammation of the oral cavity. Serious neurological side effects can occur which usually manifest as numbness or tingling of the extremities. These neurological side effects can be debilitating, are often irreversible, and necessitate stopping the Metronidazole. Serious hematological, cardiovascular, or renal complications are also common and can be life-threatening. In addition, the overgrowth of opportunistic organisms such as Candida can result from oral or intravenous metronidazole treatment. In addition, oral metronidazole can interact in an adverse manner with other medications, such as oral anticoagulants (e.g. coumadin), which can cause potentially fatal bleeding.

Topical metronidazole has previously been used for a number of skin conditions (e.g. rosacea) or as a topical vaginal preparation in the treatment of vaginal infections (e.g. trichomonas). These preparations are contained in a medium containing alcohol, which would result in stinging and burning when used on damaged skin or exposed tissue in a wound. Thus, it would be advantageous to provide a topical composition that overcomes the shortcomings of the prior art.

SUMMARY OF THE INVENTION

It is, therefore, an object of the present invention to topically apply metronidazole to treat inflammatory skin conditions; thermal, chemical or electrical burns; infections or radiation damaged skin and avoid the unwanted side effects of previous compositions and methods of administration.

Metronidazole, 2-methyl-5-nitroimidazole-1-ethanol, is a nitroimidazole derivative with activity against anaerobic protozoa, aerobic and microaerophilic bacteria, having the following structure.

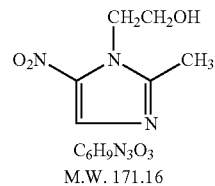

$C_6H_9N_3O_3$
M.W. 171.16

In one aspect, the present invention provides a method for treating burns comprising administering to a burn area of a subject in need thereof, a therapeutically effective amount of a composition comprising metronidazole or pharmaceutically acceptable salt thereof; and a pharmaceutically acceptable excipient.

In another aspect, the present invention relates to methods of controlling or alleviating pain by reducing the severity of inflammation and edema associated with damaged skin tissue wherein the method comprises: administering to a subject in need thereof a therapeutically effective amount of a pharmaceutical composition comprising metronidazole; and a pharmaceutically acceptable excipient, wherein said pharmaceutical composition inhibits one or more components of the inflammatory pathway.

In yet another aspect, the present invention provides a topical composition comprising metronidazole or a pharmacologically acceptable salt thereof at a concentration of about 5 wt % to about 12.5 wt % in a pharmacologically acceptable non-aqueous vehicle. The concentration of metronidazole is preferably about 10 wt %. The concentrations are based on the total weight of the composition.

The vehicle is preferably an organic vehicle and, typically, comprises at least one hydrocarbon compound. Preferably, the vehicle comprises a mixture of at least two semi-solid saturated hydrocarbon compounds. An example of a suitable vehicle is white petrolatum (USP), also known as white soft paraffin (BP). Other suitable vehicles include zinc oxide, Vaseline™, Aquaphor (a combination of mineral oil, petrolatum ceresin and lanolin), lanolin or a petroleum-based carrier.

The composition may consist essentially of metronidazole and the vehicle. However, a therapeutic amount of at least one other agent may be added to the composition to add to its effectiveness. Additional agents that may be added include steroids, e.g. hydrocortisone or a pharmacologically acceptable derivative thereof, analgesic agents, preferably from the amide or ester class such as pramoxine or benzocaine, antimicrobial agents (antibacterial or antiviral), e.g. ciprocfloxacin, amoxicillin-clavulonic acid, erythromycin, tetracycline, clindamycin or doxycyclin, substances that either promote skin integrity or inhibits skin breakdown, e.g. vitamin E, aloe, zinc oxide or other barrier cream, anti-inflammatory agents, e.g. a non-steroidal anti-inflammatory agent selected from aminosalicylic acid, ibuprofen, sulindac, piroxicam or diflunisal. The additional or supplemental antibiotic or antiviral medications may add to the antibacterial spectrum of activity (gram positive, gram negative aerobic or anaerobic, antiviral) of metronidazole.

The topical composition is preferably in a form suitable for direct application to the damaged area of the skin surface. Suitable forms include ointment, lotion, gel, foam or cream to be used for treatment of burns and skin wounds in warm-blooded animals, such as mammals and especially humans. In particular, the present invention is concerned with inflammation-associated tissue damage and is particularly directed to prophylactic and therapeutic methods for treating localized and systemic inflammation associated with burns, as well as the treatment of a variety of diseases associated with the inflammation that ensue from a burn.

Tissue damage due to burns is among the oldest, most complex and painful injuries known and damage can be very severe. Such damage can be due to thermal burns, electrical burns, chemical burns or radiation burns. Thermal burns not only damage the surface but also tissues under the skin. Electrical burns may be caused by an electric current when it passes from an electrical source to the body. This type of burn usually completely destroys and chars the skin at the current's point of entry into the body. Chemical burns can be caused by various irritants and poisons, including strong acids and alkalis, phenols and cresols (organic solvents). Radiation burns can be caused by nuclear accidents, laboratory exposure, accidents during X-ray radiation chemotherapy, and over-exposure to sun. Radiation burns can cause inflammation, edema, ulcerations, damage to underlying endothelium and other cell types, as well as mutagenesis resulting in cancer, especially hematologic malignancies.

The metronidazole compositions of the present invention may be used on different levels of burns and especially $1^{st}$ and $2^{nd}$ degree burns. For example, a $1^{st}$ degree burn includes damage from radiation, such as, sunburn or radiation cancer therapy and such damage shows the development of edema and painful erythema. $2^{nd}$ degree burns include the development of erythema, blisters and histologically, the basal membrane is partially destroyed. $3^{rd}$ and $4^{th}$ degree burns are very severe because the epidermis and dermis is totally destroyed and such burns usually require grafting of new skin.

In yet another aspect, the present invention provides a topical composition comprising metronidazole or a pharmacologically acceptable salt thereof at a concentration of about 5 wt % to about 12.5 wt %, more preferably about 10 wt %, in a pharmacologically acceptable non-aqueous vehicle for use in the topical treatment of the damaged surface skin and tissues. Notably, the metronidazole composition of the present invention relieves pain, reduces inflammation and edema, promotes wound healing and reverses tissue induration and granulation.

In another aspect, the present invention provides for the use of metronidazole or a pharmacologically acceptable salt thereof in the manufacture of a topical medicament to promote healing and relieve pain caused by damaging conditions of skin surfaces and tissues therebeneath.

In yet another aspect, the present invention provides for a method for preventing or ameliorating the adverse effects associated with controlled thermal induced skin damage employed in scar and tattoo removal, cancer excisions, cautery excision of polyps, ulcers, treatment of decubitus ulcers (bedsores), acne, and cutaneous fungal infections by administering to a subject in need thereof a therapeutically effective amount of a pharmaceutical composition comprising metronidazole or a functional derivative thereof; and a pharmaceutically acceptable excipient, wherein said pharmaceutical composition promotes rapid regeneration of damaged tissues while retaining the original composition of the tissue and minimizing complications and scarring associated with the thermally induced burn in one or more of the recited conditions.

In a further aspect, the present invention provides for methods of preventing or ameliorating blistering or pain associated with overexposure to sun, the method comprising administering to a subject in need thereof a therapeutically effective amount of a pharmaceutical composition comprising metronidazole and a pharmaceutically acceptable excipient.

In yet another aspect, the present invention provides for a method for preventing or ameliorating the deleterious inflammatory response and/or the adverse sequellae associated with controlled therapeutic thermal induced skin damage employed in the use of lasers for the treatment of medical conditions and the use of induced thermal injury in various cosmetic procedures, wherein the method comprises administering to a subject in need thereof a therapeutically effective amount of a pharmaceutical composition comprising metronidazole and a pharmaceutically acceptable excipient, wherein said pharmaceutical composition prevents or ameliorates the deleterious inflammatory response and/or the adverse sequellae associated with such controlled therapeutic thermal induced skin damage.

In a further aspect, the present invention provides the use of metronidazole or a pharmacologically acceptable derivative thereof in the manufacture of a topical medicament to treat ulcers or skin defects. The ulcers may be infective or inflammatory ulcers and may be induced by HIV or radiation. Further, the ulcers may include pressure sores, varicose ulcers, ischemic ulcers and diabetic ulcers.

The invention also encompasses methods of treatment of the above-mentioned conditions and indications using the topical composition containing metronidazole of present invention. The dose of metronidazole for each application is preferably between from about 125 mg to about 1250 mg, more preferably between from about 125 mg to about 375 mg and most preferably about 250 mg. The most preferred dose is based on a single application of 2.5 $cm^3$ of a 10 wt % metronidazole ointment. The composition is usually applied between from 2 to 4 times daily and preferably 3 times daily.

In yet another aspect, the present invention relates to kits for the treatment of burns, damaged skin, ulcers, etc., wherein the kit includes packaging that contains a composition formulated for topical application and comprising at least an effective amount of metronidazole or salt thereof in a pharmaceutically acceptable carrier.

These and other advantages and features of the present invention will be described more fully in a detailed description of the preferred embodiments which follows.

DETAILED DESCRIPTION OF THE INVENTION

Throughout the instant specification and claims, the following definitions and general statements are applicable.

As used herein, whether in a transitional phrase or in the body of a claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a composition, the term "comprising" means that the composition includes at least the recited features or components, but may also include additional features or components.

The terms "consists essentially of" or "consisting essentially of" have a partially closed meaning, that is, they do not permit inclusion of steps or features or components which would substantially change the essential characteristics of a process or composition; for example, steps or features or components which would significantly interfere with the desired properties of the compositions described herein, i.e., the process or composition is limited to the specified steps or materials and those which do not materially affect the basic and novel characteristics of the invention.

The terms "consists of" and "consists" are closed terminology and allow only for the inclusion of the recited steps or features or components.

As used herein, the singular forms "a," "an" and "the" specifically also encompass the plural forms of the terms to which they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 10%.

As used herein, "treating" means reducing, hindering or inhibiting the development of, controlling, alleviating and/or reversing the symptoms in the individual to which a combination or composition of the invention has been administered, as compared to the symptoms of an individual not being treated according to the invention. A practitioner will appreciate that the combinations, compositions, dosage forms and methods described herein are to be used in concomitance with continuous clinical evaluations by a skilled practitioner to determine subsequent therapy.

Without wishing to be bound by any particular theory, it is believed that the use of metronidazole by direct application to the diseased or otherwise affected is primarily a local effect. Minimal systemic absorption is observed and therefore systemic side effects are effectively reduced or eliminated. As such, the dose of metronidazole can be altered for specific tissue and applied directly to the diseased or otherwise effected area thereby increasing the efficacy of the medication.

The topical compositions of the present invention are generally cream or viscous suspensions having at least one active ingredient and at least one additional component including preservatives, chelating agents, surfactants, thickeners, thickeners-solubilizers, buffers, co-solvents, or lubricants.

According to one embodiment of the present invention, the pharmaceutical composition takes the form of a cream, ointment or foam suspension that is applied topically to a damaged skin surface. The formulations comprise metronidazole dissolved or dispersed in a suitable flowable carrier vehicle. The formulation can be thickened with one or more thickeners, can contain a buffer, and can also comprise an effective amount of a lubricant such as a natural or synthetic fat or oil, e.g. a tris-fatty acid glycerate or lecithin. Non-toxic non-ionic surfactants can also be included as wetting agents and dispersants. Preferably, the composition does not include an alcohol because of the painful effect caused by alcohol on damaged skin. Further, the pH of the composition is preferably 5.5 to 8.5, and more preferably a pH of about 7.

The composition according to the present invention may also comprise additional pharmaceutically acceptable compounds and/or compositions. It is thus to be understood that all the additional compounds and/or compositions mentioned below have to be physiologically acceptable.

The composition according to the present invention may be topically applied as such within a suitable carrier, solvent, dissolvent, extract, solutions e.g. oily, suspension; microemulsion, vesicles, etc. Where employed, the carrier is inert in the sense of not bringing about a deactivation or oxidation of the metronidazole, and in the sense of not bringing about any adverse effect on the skin areas to which it is applied.

In one aspect of the invention, the metronidazole is applied in admixture with a dermatologically acceptable carrier or vehicle (e.g., as a lotion, cream, ointment, soap or the like) so as to facilitate topical application and, in some cases, provide additional therapeutic effects as might be brought about, e.g., by moisturizing of the affected and/or damaged skin. The metronidazole carrier for dermatological compositions preferably comprises a carrier which will form a film or layer on the skin to which it is applied so as to localize the application and provide some resistance to washing off by immersion in water or by perspiration.

Many preparations are known in the art, and include lotions containing oils and emollients such as hydrocarbon oils and waxes, silicone oils, vegetable, animal or marine fats or oils, glyceride derivatives, fatty acids or fatty acid esters, lanolin and derivatives, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, by utilization of different proportions of the ingredients and/or by inclusion of thickening agents such as gums or other forms of hydrophilic colloids.

Various types of other ingredients may be present in the metronidazole compositions of the present invention. For example, sunscreens may be included such as those materials commonly employed to block ultraviolet light. Illustrative compounds are the derivatives of PABA, cinnamate and salicylate. The exact amount of sunscreen employed in the compositions can vary depending upon the degree of protection desired from the sun's UV radiation.

The compositions for use in the methods of the present invention may include components suitable as carriers, such as starches, emollients, sugars, microcrystalline cellulose, diluents, granulating agents, lubricants, surfactants including amphoteric, binders, disintegrating agents, and the like, with the topical preparations being preferred.

Emollients are often incorporated into the therapeutic compositions of the present invention. Levels of such emollients may range from about 0.5% to about 60%, preferably between about 5% and 30% by weight of the total composition. Emollients may be classified under such general chemical categories as esters, fatty acids and hydrocarbons. Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate.

Suitable fatty acids include those compounds having from 10 to 20 carbon atoms. Especially preferred are compounds such as cetyl, arachidyl, behenyl, cetearyl, myristyl, palmitic and stearyl acids.

Exemplary hydrocarbons which may serve as emollients are those having hydrocarbon chains anywhere from 12 to 30 carbon atoms. Specific examples include mineral oil, petroleum jelly, paraffin oil, squalene and isoparaffins.

Another category of functional ingredients within the therapeutic compositions of the present invention are thickeners. A thickener will usually be present in amounts anywhere from 0.1% to 20% by weight, preferably from about 0.5% to 10% by weight of the composition. Exemplary thickeners are cross-linked polyacrylate materials. Gums may be employed such as xanthan, carrageenan, gelatin, karaya, pectin and locust beans gum. Under certain circumstances the thickening function may be accomplished by a material also serving as a silicone or emollient. For instance, silicone gums having a viscosity in excess of 10 mPas and esters such as glycerol stearate have dual functionality.

Still further, the therapeutic compositions of the present invention may include preservatives, moisturizers, surfactants, antimicrobials, etc. Preservatives may include tetrasodium ethylene-diamine tetraacetic acid (EDTA), methylparaben, benzophenone-4, methylchloroisothiazolinone, sodium benzoatemethylisothiazolinone, and the like, and mixtures thereof. Preservatives, when used, are typically present in an amount from about 0.01% to 10% weight, preferably about 0.05% to 4% weight, and more preferably, from about 0.1% to 2% weight.

Preferred moisturizers may include wheat protein (e.g., laurdimonium hydroxypropyl hydrolyzed wheat protein), hair keratin amino acids, sodium peroxylinecarbolic acid, panthenol, tocopherol (Vitamin E), dimethicone, arachidylglucoside and the like, and mixtures thereof. Moisturizers, when used, are typically present in an amount from about 0.01% to 10% weight, preferably about 0.05% to 1.5% weight, more preferably, from about 0.1% to 1% weight of the composition.

Preferred surfactants, including both the foaming and non-foaming type, include sodium laureth sulfate, sodium laureth-13 carboxylate, disodium laureth sulfosuccinate, disodium cocoamphodiacetate, glycol stearate, PEG-150 distearate and the like, and mixtures thereof. More preferably, at least one amphoteric surfactant is included in the composition, selected from the group consisting of lauroamphocarboxypropionate, lauroamphopropionate, lauroamphoglycinate, lauroamphocarboxyglycinate, lauroamphopropyl sulfonate, lauroamphocarboxypropionic acid, myristoamphocarboxy-propionate, myristoamphopropionate, myristoamphoglycinate, myristoamphocarboxyglycinate, myristoamphopropylsulfonate, myristoamphocarboxypropionic acid, cocoamphocarboxypropionate, cocoamphopropionate, cocoamphoglycinate, cocoamphocarboxyglycinate, cocoamphopropylsulfonate, cocoamphocarboxypropionic acid and mixtures thereof. The surfactant component may be present in an amount from about 0.1% to about 20% weight of the composition.

The compounds of the present invention include pharmaceutically acceptable salts that can be prepared by those of skill in the art. As used herein, by "pharmaceutically acceptable salt" it is meant those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art, such as hydrochloride, hydrobromide, mesylate, acetate, trifluoroacetate, propionate, fumarate, tartrate, citrate, phosphate, succinate, bisulfate, etc. For example, S. M Berge, et al. describe pharmaceutically acceptable salts in detail in *J. Pharmaceutical Sciences,* 1977, 66: 1-19.

The topical skin treatment composition of the invention can be formulated as a lotion having a viscosity of from 4,000 to 10,000 mPas, a fluid cream having a viscosity of from 10,000 to 20,000 mPas or a cream or a gel having a viscosity of from 20,000 to 100,000 mPas or above.

The metronidazole composition can be packaged in a suitable container to suit its viscosity and intended use by the consumer. For example, a lotion or fluid cream can be packaged in a bottle, a propellant-driven aerosol device or a container fitted with a pump suitable for finger operation. When the composition is a cream, it can simply be stored in a non-deformable bottle or squeeze container, such as a tube or a lidded jar.

Generally, in the practice of methods of the invention, the composition is topically applied to the damaged skin area in a predetermined or as-needed regimen either at intervals by application of a lotion or the like, it generally being the case that gradual improvement is noted with each successive application.

Because of its ease of administration, a cream, lotion, gel or ointment represents the most advantageous topical dosage unit form, and such forms may be prepared as rinse-off or leave-on products, as well as two stage treatment products for use with other skin cleansing or managing compositions. Each of these forms is well understood by those of ordinary skill in the art, such that dosages may be easily prepared to incorporate the pharmaceutical composition of the invention.

In general, the compositions of the present invention are intended to be applied topically and directly to the burns or wound as described above. When the wound is deep, or the burn severe, it is preferred that the composition is in the form of an ointment, salve or cream which is spread directly onto the wound and then covered with a standard sterile dressing pad or other appropriate dressing material. Alternatively, the ointment, cream or salve of the present composition is applied directly onto the dressing pad or other appropriate dressing material. The pad or dressing material is then placed over the wound or burn with the medicine-side down. This latter approach works better when applying dressing to severe burns and shallow wounds.

Thus, the pharmaceutical composition of the present invention is applied to a wound so as to cover the injured surface completely. Dressing-change schedules are of course dictated by the condition of the wound. Dressings are advantageously changed three to four times a day. Repeated daily dressing changes are continued until the wound or burn is healed. Healing time varies, depending upon the type and depth of the wound or the severity of the burn.

The present pharmaceutical composition is effective in the treatment of a large variety of wounds and burns to a mammal, subject or patient in need thereof where bacterial and fungal contamination would ordinarily occur in the absence of treatment.

The present medicinal composition can of course also be used to treat burns and wounds in other mammals, such as veterinary animals including, without limitation, dogs, cats, other household pets, horses, farm animals, and the like. The magnitude of a prophylactic or therapeutic dose of the pharmaceutical composition of the invention in the acute or chronic management of pathology and pain associated with above-mentioned indications will vary with the severity of the condition to be treated and the route of administration.

The dose, and perhaps the dose frequency, will also vary according to the age, body weight, and response of the individual.

Actual dosage levels of active ingredients in the pharmaceutical compositions of this invention may be varied so as to obtain an amount of the active compound(s) that is effective to achieve the desired therapeutic response for a particular patient, compositions, and mode of administration. It is within the skill of the art to start doses of the pharmaceutical compound at levels lower than required to achieve the desired therapeutic effect and to gradually increase the dosage until the desired effect is achieved.

Example 1

Method of Production of the Composition 100 g of metronidazole powder (USP) was mixed with 900 g of white petrolatum (USP) and the mixture passed through a mixer known as an "ointment mill" to produce a 10 wt % metronidazole composition having a "fluffy" texture.

Example 2

Treatment for Radiation Damage

Because of metronidazole's unique spectrum, it has additional anti-inflammatory properties, possibly as a result of free radical scavenging, and is effective in non infective inflammatory processes, such as thermal burns and radiation burns. Metronidazole is therefore effective in the treatment of radiation burns, radiation dermatitis or radiation ulcers.

Topical 10% metronidazole is effective in treating radiation burns, radiation dermatitis or radiation ulcers after external beam radiation for cancer.

A 54 year old male underwent neoadjuvant chemoradiation with flouro uracil and 4500 rads of external beam radiation for a T3 N1 adenocarcinoma of the rectum. The patient experienced severe perianal erythema, induration and pain due to the radiation. Topical 10% metronidazole was applied to the area, and after 72 hours he experienced significant pain relief and resolution of the erythema and induration.

A 54 year old female received external beam radiation for a T3 N1 adenocarcinoma of the breast with axillary lymph node involvement. She experienced severe radiation dermatitis in the axillary and chest area. Topical 10% metronidazole was applied to the skin area exposed to the radiation and after 5 days she experienced significant resolution of the erythema and induration.

Thermal or radiation burns from solar radiation (sunburn) and thermal burns (first, second, third, or fourth degree) may be treated with the metronidazole composition of the present invention.

A 14 year old boy developed severe sunburn over his upper arms after spending a weekend swimming in a local lake without adequate sun block. Topical 10% metronidazole was applied to the sunburned area, and after 24 hours he experienced significant pain relief and resolution of the erythema.

Example 3

Hidradenitis

A 34 year old male presents with Hidradenitis in both groins. Topical 10% metronidazole was applied to the area of damage. After 4 weeks, the induration and discharge were decreased significantly.

Fistula in Ano/Perianal Abscess

A 24 year old female underwent incision and drainage of a perianal abscess. The abscess cavity is typically slow to heal. Topical 10% metronidazole was applied and after 2 weeks the cavity had closed and epithelialized.

Thrombosed External Hemorrhoid

A 34 year old presents with a thrombosed external hemorrhoid after planting trees in his yard. The thrombus measured 2 cm diameter, and the patient declined excision. Topical 10% metronidazole was applied to the area and after 1 week, the thrombus had almost entirely resolved.

Pyoderma Gangenosum

A 34 year old with Crohn's disease presents with Pyoderma gangenosum over the pretibial area. Topical 10% metronidazole was applied to the area and after 4 weeks, the ulcer had contracted to 50% of its original size.

Perineal Sinus (Post-Proctectomy for Cancer or Crohn's Disease)

A 54 year old presents with a perineal sinus after proctectomy for Crohn's proctitis. The patient experienced pain and discharge. Topical 10% metronidazole was applied to the area and after 4 weeks, the discharge had ceased and the sinus had closed.

Example 4

Treatment after Post-Operative Anorectal Surgery

Because of its gram-negative anaerobic spectrum, topical metronidazole is also ideal for applying to perianal incisions after surgery. Its effectiveness has been demonstrated after surgical hemorrhoidectomy, but it is also effective for any perianal/perineal operation, such as a fissurectomy/sphincterotomy.

A 34 year old female experienced pain and bleeding from a fissure in ano. Fiber supplements failed to heal the fissure. Topical 10% metronidazole was applied to the area and after 3 weeks, the patient's pain had resolved and bleeding had ceased.

Non Healing Surgical Incisions

A 54 year old underwent a low anterior resection for a rectal cancer. The patient is obese and is a heavy smoker. He developed a chronic wound infection in his midline incision. The wound was debrided and topical 10% metronidazole was applied to the area and after 4 weeks, the wound had closed and epithelialized.

Excision Pilonidal Sinus

A 34 year old male had persistent pain and discharge after excision of a pilonidal sinus. A chronic ulcer remained. The wound was debrided and topical 10% metronidazole was applied to the area. After 4 weeks, the ulcer had closed and pain and discharge were resolved completely.

Example 5

Effective Treatment of Skin Ulcers

Gram-negative anaerobic bacteria are also the major pathogens in ischemic/decubitus ("pressure sores") or diabetic skin ulcers.

Decubitus Ulcers ("Pressure Sores" or "Bed Sores")

A 79 year old nursing home patient developed a decubitus ulcer in the pre-sacral area. The ulcer was surgically debrided and topical 10% metronidazole was applied to the area. After 4 weeks, the ulcer had contracted to 50% of its original size and eschar was significantly reduced.

Varicose Ulcers (Due to Varicose Veins)

A 60 year old female presents with chronic varicose ulcers over the medal malleolus. Compression therapy failed to heal the ulcers. Topical 10% metronidazole was applied to the area. After 6 weeks, the ulcer had contracted to 75% of its original size and induration was significantly reduced.

Ischemic Ulcers (Peripheral Vascular Disease)

A 58 year old male presents with chronic peripheral vascular disease and ischemic ulcers over the medial aspect of the hallux. The drug Trental failed to improve healing and he had already undergone emoral-tibial bypass. Topical 10% metronidazole was applied to the area. After 4 weeks, the ulcer had contracted to roughly 50% of its original size and necrotic tissue was significantly reduced.

Diabetic Ulcers

A 68 year old male presents with chronic type 2 diabetes and a non healing ulcer over the lateral aspect of the fore foot. Topical 10% metronidazole was applied to the area. After 6 weeks, the ulcer had contracted to roughly 50% of its original size and necrotic tissue was significantly decreased.

That which is claimed is:

1. A method of relieving pain and/or promoting wound healing in a patient due to a pilonidal sinus wound, hidradenitis or pressure sore wounds, the method comprising:
applying to the damaged skin area a topical composition, wherein the topical composition consists essentially of (a) metronidazole in a therapeutically effective concentration of 10 wt % to treat the pilonidal sinus wound, hidradenitis or pressure sore wounds and (b) a pharmacologically acceptable non-aqueous vehicle.

2. The method of claim 1, wherein said vehicle is an organic vehicle.

3. The method of claim 1, wherein the vehicle comprises at least one hydrocarbon compound.

4. The method of claim 1, wherein the vehicle comprises a mixture of at least two semi-solid saturated hydrocarbon compounds.

5. The method of claim 1, wherein the vehicle comprises white petrolatum (USP).

6. The method of claim 1, wherein said topical composition is in the form of an ointment, lotion, gel, foam or cream.

7. The method of claim 1, wherein metronidazole is applied at a dosage for each application from about 125 mg to about 1250 mg.

8. The method of claim 7, wherein the dosage of metronidazole for each application is from about 125 mg to about 375 mg.

9. The method of claim 8, wherein the dosage of metronidazole for each application is about 250 mg.

10. The method of claim 1, wherein said topical composition is applied between from 2 to 4 times daily.

11. The method of claim 1, wherein said topical composition has a fluffy texture.

12. The method of claim 11, wherein said topical composition is obtained by passing metronidazole and white petrolatum through an ointment mill.

* * * * *